US010251809B2

(12) United States Patent
Graindorge et al.

(10) Patent No.: US 10,251,809 B2
(45) Date of Patent: Apr. 9, 2019

(54) DEVICE FOR THE TREATMENT OF SLEEP APNEA SYNDROME IN A PATIENT BY KINESTHETIC STIMULATION

(71) Applicants: SORIN CRM SAS, Clamart (FR); INSERM—INSTITUT NATIONAL DE LA SANTE ET DE LA RECHERCHE MEDICALE, Paris (FR); UNIVERSITÉ DE RENNES 1, Rennes (FR); UNIVERSITE JOSEPH FOURIER—GRENOBLE 1, Grenoble (FR)

(72) Inventors: Laurence Graindorge, Thouaré sur Loire (FR); Amel Amblard, Sceaux (FR); Christine Henry, Paris (FR); Marcel Limousin, Paris (FR); Laure Duchemin Laporte, Morangis (FR); Alfredo Hernandez, Cesson Sévigné (FR); Jean-Louis Pépin, Grenoble (FR)

(73) Assignees: Sorin CRM SAS, Clamart (FR); INSERM—INSTITUT NATIONAL DE LA SANTE ET DE LA RECHERCHE MEDICALE, Paris (FR); UNIVERSITÉ DE RENNES 1, Rennes (FR); UNIVERSITE JOSEPH FOURIER—GRENOBLE 1, Grenoble (FR)

( * ) Notice: Subject to any disclaimer, the term of this patent is extended or adjusted under 35 U.S.C. 154(b) by 1026 days.

(21) Appl. No.: 14/617,534

(22) Filed: Feb. 9, 2015

(65) Prior Publication Data
US 2015/0224018 A1    Aug. 13, 2015

(30) Foreign Application Priority Data
Feb. 11, 2014 (FR) .................................. 14 51061

(51) Int. Cl.
*A61H 23/00* (2006.01)
*A61B 5/00* (2006.01)
(Continued)

(52) U.S. Cl.
CPC ............. *A61H 23/00* (2013.01); *A61B 5/024* (2013.01); *A61B 5/4812* (2013.01);
(Continued)

(58) Field of Classification Search
CPC .......... A61H 39/002; A61H 2201/0157; A61H 2203/0456; A61H 2205/027; A61H 2230/04; A61H 2230/045
See application file for complete search history.

(56) References Cited

U.S. PATENT DOCUMENTS

| 4,813,427 A | 3/1989 | Schlaefke et al. |
| 2004/0215236 A1 | 10/2004 | Lattner et al. |

(Continued)

FOREIGN PATENT DOCUMENTS

| EP | 1 317 943 | 6/2003 |
| EP | 1 319 421 | 6/2003 |

(Continued)

OTHER PUBLICATIONS

Beuchee et al., "Automatic kinesthetic-stimulation related to apnea-bradycardia detection in premature infants", ITBM-RBM, 28(2007) 124-130.
(Continued)

*Primary Examiner* — Rachel T Sippel
(74) *Attorney, Agent, or Firm* — Foley & Lardner LLP

(57) ABSTRACT

A device for treating sleep apnea in a patient through stimulation. The device includes a generator configured to produce stimulation pulses, a stimulator that receives the stimulation pulses produced by the generator and delivers stimulation to the patient, and a controller. The controller is
(Continued)

configured to determine a sleep state of the patient, adaptively control the generator based on the sleep state where the sleep state includes a plurality of sleep stages, and modulate a stimulation energy of the stimulation pulses produced by the generator based on the sleep stage of the patient.

20 Claims, 5 Drawing Sheets

(51) Int. Cl.
*A61B 5/024* (2006.01)
*A61H 23/02* (2006.01)

(52) U.S. Cl.
CPC .......... *A61B 5/4818* (2013.01); *A61H 23/02* (2013.01); *A61H 2201/10* (2013.01); *A61H 2201/165* (2013.01); *A61H 2201/5058* (2013.01); *A61H 2230/04* (2013.01); *A61H 2230/06* (2013.01); *A61H 2230/105* (2013.01)

(56) References Cited

U.S. PATENT DOCUMENTS

| | | | |
|---|---|---|---|
| 2008/0009915 A1 | 1/2008 | Moses et al. | |
| 2008/0242956 A1 | 10/2008 | Suzuki et al. | |
| 2009/0192556 A1* | 7/2009 | Wu | A61B 5/0031 607/3 |
| 2010/0076251 A1 | 3/2010 | Stasz et al. | |
| 2010/0087701 A1* | 4/2010 | Berka | A61M 21/02 600/27 |
| 2012/0089199 A1* | 4/2012 | Bolea | A61N 1/0556 607/42 |
| 2013/0102937 A1 | 4/2013 | Ehrenreich et al. | |
| 2014/0088378 A1* | 3/2014 | Muzet | A61B 5/02125 600/301 |

FOREIGN PATENT DOCUMENTS

| | | |
|---|---|---|
| EP | 1 433 496 | 6/2004 |
| EP | 1 584 288 | 10/2005 |
| EP | 2 465 434 | 6/2012 |
| WO | WO-2007/141345 | 12/2007 |
| WO | WO-2009/154458 | 12/2009 |

OTHER PUBLICATIONS

Hord D. et al., "The Evoked Heart Rate Response during Sleep", Psychophysiology, 3:46-54 (1966), 10 pages.

Pichardo et al., "Validation of a Vibrotactile Stimulation System to Treat Apnea of Prematurity", Proceedings of the IEEE 27th annual Northeast Bioengineering Conference, University of Connecticut, Storrs, CT (2001) pp. 13-14, 2 pages.

Preliminary Search Report for French Application No. FR 1451061, dated Aug. 6, 2014, 1 page.

* cited by examiner

DEVICE FOR THE TREATMENT OF SLEEP APNEA SYNDROME IN A PATIENT BY KINESTHETIC STIMULATION

CROSS REFERENCE TO RELATED APPLICATIONS

This application claims the benefit of and priority to French Patent Application No. 14/51061, filed Feb. 11, 2014, which is hereby incorporated by reference herein in its entirety.

BACKGROUND

The invention relates to the diagnosis and treatment of sleep disorders. It more particularly relates to the use for this purpose of a device known as "kinesthetic stimulation" device, that is to say a device with external sensory stimulation of the patient by methods of a vibrator in contact with skin in a sensitive, specific area of the body of the patient. Enabling this vibrator has the effect of locally exciting cutaneous endings or mechanical receptors in the skin and triggering a response of the autonomic nervous system of the patient, with sympathetic predominance (hereinafter "autonomic response").

Autonomic response to sympathetic activation is observable on major modulator effects of cardiac activity, for example:
Chronotropic effect: increased heart rate, or decrease in RR intervals;
Inotropic effect: increased cardiac contractility.

This autonomic response is also observed on the peripheral vasoconstriction, which is increased in case of sympathetic autonomic activation. This phenomenon may be implemented notably with the device described in US 2013/0102937 A1, which proposes to treat hypertension by appropriate stimulation of baroreceptors or nerves, especially during periods when the patient is asleep. The stimulation is triggered when the patient is known to be dormant, then maintained at a constant level. In addition to these effects on cardiac activity, sympathetic activation causes responses in the respiratory system or in the central nervous system (autonomic awakenings).

This is a noninvasive method which is applicable for a number of sleep disorders as an alternative to conventional therapeutic approaches based on the application of a continuous positive airway pressure through a face mask (processing named CPAP), the use of a mandibular protrusion splint and/or electrical stimulation of the hypoglossal nerve, which involves an implant such as a pacemaker.

In particular, the respiratory disease known as "sleep apnea syndrome" (SAS) is characterized by the frequent occurrence (at least 10 to 20 times per hour) of apneas during a sleep phase of the patient, an "apnea" (or pause in breathing) being defined as a temporary cessation of the respiratory function for a duration of more than 10 seconds. It may also be characterized by the occurrence in the same conditions of hypopnea, a "hypopnea" being defined as a significant decrease (but without interruption) of the respiratory rate, typically a decrease of over 50% compared to an earlier reference mean. In the following of the description, we will not distinguish between these two phenomena, a reference to "apneas" being meant to also include hypopneas.

This condition reached more than 4% of the population and over 50% of patients with heart failure. To protect the individual against asphyxiation due to the decrease of oxygen concentration in the blood during the interruption or reduction of the respiratory rate, the body adapts but with a deleterious effect on sleep, causing unconscious microawaking. Daytime sleepiness, with loss of attention and increased risk of accident, follows in phase of awakening. Furthermore, several studies of patients with SAS have shown greater incidence of disorders such as arterial hypertension, ventricular arrhythmias, myocardial infarction and heart failure.

For stopping the apnea episodes with a stimulation therapy, US2008/0009915 A1 proposes an acoustic stimulation therapy, US2004/0215236 A1 a vestibular stimulation therapy, WO2009/154458 A1 an electrical stimulation therapy and the U.S. Pat. No. 4,813,427A the application of a gas in parallel to tactile stimulation therapy. Kinesthetic stimulation has been proposed in the past to minimize or stop the episodes of sleep apnea in adults or in the newborn, as described for example in the WO 2007/141345 A1 (FR 2908624 A1).

These techniques are also described in the articles of Pichardo R., et al., "Validation of a Vibrotactile Stimulation System to Treat Apnea of Prematurity", *Proceedings of the IEEE 27th annual Northeast Bioengineering Conference,* University of Connecticut, Storrs, Conn. (2001) 13-14, and Beuchée A. et al., "Stimulateur kinesthésique automatisé asservi à la détection d'apnées-bradycardies chez le nouveau-né prématuré", *ITBM-RBM,* 28(2007) 124-130.

The first drawback of these stimulation methods is the response variability according to the patient, or even depending on the patient's condition and in particular the sleep state. This variability may require complex initialization methods of the system to adapt to the patient parameters. The second drawback is a phenomenon of habituation, which requires therapy to constantly evolve to keep it effective. Some systems describe a randomized variation of the therapy, which then may be poorly reproducible. The third drawback is the risk of waking the patient. Indeed, the stimuli can generate awakenings in turn responsible for the sleep destructuration. These awakenings induce a loss of much of the benefit of therapy. But few methods take into account this risk, or describe an impractical method for example based on the detection of sleep states by analyzing the EEG, a technique which is impractical in routine practice or at home.

SUMMARY

Kinesthetic stimulation therapy of this disease includes, on detection of an apnea or hypopnea episode, generating appropriate stimulation which can cause an autonomic response in the patient that may trigger respiratory modification, for example, a respiratory recovery or an increase in respiration that will end apnea. Thus, according to various embodiments, there is disclosed a technique to interrupt episodes of apnea by kinesthetic stimulation, by generating a sufficient but not excessive autonomic response adapted to stop the apnea, in order to limit the appearance of microawakenings.

In this regard, clinical studies have shown that for a given stimulation energy, the autonomic response is dependent on the sleep stage (slow sleep stages I to IV and REM sleep). See for example Hord D. et al., "The Evoked Heart Rate Response during Sleep", *Psychophysiology,* 3:46-54 (1966), which examines various parameters of the change in autonomic response of patients when sound stimuli are emitted close to their ear at different times of sleep.

According to an exemplary embodiment, in view of the relationship between the sleep stage and the autonomic response, the kinesthetic stimulation therapy is directed to i) detecting the current sleep stage and ii) controlling the kinesthetic stimulation energy according to the current sleep stage thus detected at the time when the stimulation is applied, to generate sufficient autonomic response to stop apnea but the level of which is low enough to prevent or at least limit the appearance of micro-awakenings.

According to various embodiments, a first aspect of a method to automatically determine the current sleep stage of the patient includes (but not limited to) the application for a kinesthetic stimulation therapy to the appropriate energy level, as just exposed, or any other therapy (cardiac pacing, neuromuscular stimulation, etc.), differentially depending on the current sleep stage at the time of application of the therapy. This discrimination of sleep stages can also be used just for diagnostics. The discrimination can be used to provide a less expensive and more convenient alternative to polysomnography (PSG). The discrimination can be used to analyze sleep patterns and diagnose certain sleep disorders.

The sleep stages may be manually, sometimes automatically, evaluated from electroencephalographic recordings (EEG) signals collected during polysomnography, by analyzing the amplitude and frequency of at least three channels of EEG signals. The difficulty is related to the placing of many EEG sensors, which makes such an examination not feasible in routine. Other methods of detection of sleep stages have been proposed using cardiopulmonary Holter recordings, from the variability of sinus rhythm, etc., but these methods do not allow to differentiate between wakefulness and sleep state, or between REM state (REM) and non-REM state (slow wave sleep), and they do not distinguish all sleep stages, especially to discriminate between the different slow wave sleep stages, from I (drowsiness) to IV (deep sleep).

Automatic discrimination of sleep stages may in particular allow a better diagnosis of sleep, because during PSG, the patient poorly sleeps insofar as he/she is in a hospital room and is covered with all kinds of sensors. Therefore there is a need for a lighter and automatic system allowing both the patient to sleep better and to provide the physician with a faster and less expensive, easily and routinely applicable method.

According to various embodiments, a second aspect relates to the use of the knowledge of the sleep current stage—whether it has been determined in accordance with the first aspect or by another method—to apply kinesthetic stimulation therapy at an appropriate energy level. The energy level is differentiated based on the current sleep stage at the time of application of the therapy in order to generate sufficient autonomic response to stop apnea but the level being low enough to prevent or at least limit the appearance of micro-awakenings.

According to an exemplary embodiment, the device/system provides for discrimination of the successive sleep stages of a patient. This device may be similar to that shown, for example, from the aforementioned articles from Pichardo et al. and Beuchée et al. The device includes a generator capable of producing controlled kinesthetic stimulation pulses bursts; at least one kinesthetic effector adapted to be applied to an external skin site of the patient, and including a vibrating electromechanical transducer adapted to receive the pulses produced by the generator; methods for measuring at least one control parameter of the current autonomic activity of the patient; and detector methods, adapted to determine a sleep state of the patient.

The device further includes, to operate the discrimination of the successive sleep stages, methods of analysis of the sleep, conditionally activated in the presence of only a sleep state determined by the detection methods and including: control methods capable of controlling the activation of the generator to trigger the production of a kinesthetic pulses burst; methods adapted to determine, according to said measurement of at least one control parameter for the current patient's autonomic activity, a variation of this control parameter subsequent to said production of the kinesthetic pulses burst; and evaluator methods suitable for determining a patient's response to autonomic kinesthetic stimulation in accordance with said variation.

According to exemplary embodiments, the sleep analysis methods include methods of discrimination, capable of determining, following the kinesthetic stimulation produced by the activation of the generator by the control methods, and in accordance with the determined autonomic response by the evaluator methods, the sleep stage of the patient from a plurality of predetermined stages of the group including: Slow Wave Sleep I, Slow Wave Sleep II, Slow Wave Sleep III, Slow Wave Sleep IV and REM sleep.

According to various embodiments:

The control parameter of the current autonomic activity of the patient is the current heart rate of the patient, or a parameter of the group including: respiratory rate; blood oxygen saturation; and derivative parameter from a phonocardiographic waveform signal or an endocardial acceleration signal;

The apparatus further includes initialization methods adapted, on determination of a sleep state by the detection methods, to establish the level of at least one predetermined parameter of the pulses burst of kinesthetic stimulation, this stimulation parameter being a parameter of the group including: delivered energy; duration of the stimulation pulses burst; pulse repetition frequency; and unitary duration of the pulses;

The initialization methods include test methods including: methods adapted to initialize the stimulation parameter level to a default value; methods able to compare the current autonomic response determined by the evaluator methods to a first threshold; and methods adapted, if the current autonomic response is below the first threshold, to iteratively change step by step the stimulation parameter level until crossing of the first threshold;

The device further includes methods adapted to reiteratively activate the methods of analysis of sleep and including: methods adapted to compare the current autonomic response with a previous stored value of the autonomic response; and methods adapted to re-activate the discriminating methods if the difference between the current autonomic response and the previous autonomic response exceeds a second predetermined threshold;

The discriminating methods are adapted to determine the sleep stage in a relative manner, with respect to a previous stored level of sleep stage of the patient, based on the determined difference between the current autonomic response and the stored previous autonomic response;

The discriminating methods are deterministic methods, able to raise the level of sleep stage in case of reduction of the gap between the current autonomic response and the previous autonomic response, and vice versa, or stochastic methods implementing an automaton with a finite number of states whose transitions are defined by a Markov or semi-Markov process.

According to the aforementioned second aspect, the invention provides a device for treatment of sleep apnea syndrome in a patient by kinesthetic stimulation, similar to that, for example, in US 2013/0102937 A1. The device includes a generator capable of producing kinesthetic stimulation controlled pulses bursts; at least one kinesthetic effector adapted to be applied to an external skin site of the patient, and including a vibrating electromechanical transducer adapted to receive the pulses produced by the generator and to provide given kinesthetic stimulation energy; and detector methods, adapted to determine a sleep state of the patient. The device further includes methods for adaptively controlling the generator, conditionally activated only in the presence of a sleep state determined by the detection methods.

According to exemplary embodiments, the methods of adaptive control of the generator include: discriminating methods, able to determine the sleep stage of the patient from a plurality of predetermined stages of the group including: Slow Wave Sleep I, Slow Wave Sleep II, Slow Wave Sleep III, Slow Wave Sleep IV and REM sleep; and modulating methods capable of changing the energy level of kinesthetic stimulation bursts produced by the generator according to the sleep stage of the patient determined by discriminating methods.

According to various embodiments:
The modulating methods may be adapted to increase the stimulation energy for a higher sleep stage, and vice versa;
The device further includes methods for detecting the occurrence of an apnea or hypopnea episode and methods adapted to conditionally activate the generator upon detection of an episode of apnea or hypopnea and possibly methods for detecting the end of the episode of apnea or hypopnea and methods able to disable the generator to detect the end of the episode of apnea or hypopnea;
The modulating methods include methods capable of applying a predetermined stimulation energy increment/decrement according to each of the predetermined sleep stages;
The modulating methods include a lookup table assigning a predetermined stimulation energy level to each of the predetermined sleep stages, and optionally methods adapted for initializing, upon determination of a sleep state by the detection methods, to establish the energy level values of the correspondence table;
The device further includes evaluator methods, capable of determining an autonomic patient's response to kinesthetic stimulation depending on the variation, following the production of the pulses burst, of a control parameter of the current autonomic activity of the patient;
The control parameter of the current autonomic activity of the patient is the patient's current heart rate or a parameter of the group comprising: breath rate; blood oxygen saturation; and derivative parameter of a phonocardiographic signal or of an endocardial acceleration signal;
The initialization methods include, for determining the energy level value of corresponding to the first sleep stage: methods able to initialize the stimulation energy to a predetermined default minimum value; methods able to compare the current autonomic response determined by the evaluator methods to a first threshold; methods capable, if the current autonomic response is below the first threshold, to step by step and iteratively change the stimulation energy until crossing of the first threshold; and methods, for the first sleep stage, for storing the value of the stimulation energy obtained after crossing the threshold;
The device further includes methods suitable for calculating and storing stimulation energy values corresponding to the sleep stages following the first stage, according to the stimulation energy value stored for the first stage;
The discriminating methods are adapted to determine the current sleep stage based on the autonomic response determined by the evaluator methods.

One embodiment relates to a device for treating sleep apnea in a patient through stimulation. The device includes a generator configured to produce stimulation pulses, a stimulator that receives the stimulation pulses produced by the generator and delivers stimulation to the patient, and a controller. The controller is configured to determine a sleep state of the patient, adaptively control the generator based on the sleep state where the sleep state includes a plurality of sleep stages, and modulate a stimulation energy of the stimulation pulses produced by the generator based on the sleep stage of the patient.

According to an exemplary embodiment, the generator is activated by the controller in the presence of the sleep state. The plurality of sleep stages include slow-wave sleep I, slow-wave sleep II, slow-wave sleep III, slow-wave sleep IV, and REM sleep. In some embodiments, the controller is configured to increase the stimulation energy as the sleep stage increases, and decrease the stimulation energy as the sleep stage decreases.

In some embodiments, the device includes a sensor configured to detect an occurrence of an apnea or hypopnea episode. The controller activates the generator upon detection of the apnea or hypopnea episode and disables the generator on the detection of the end of the apnea or hypopnea episode.

In various embodiments, the controller modulates the stimulation energy based on a predetermined increment/decrement for each of the plurality of sleep stages. In other embodiments, the controller utilizes a correspondence table to assign the stimulation energy to each of the plurality of sleep stages.

In some embodiments, the controller determines a response of the patient to the stimulation based on the variation of a biological parameter of the patient following the delivery of the stimulation to the patient. The biological parameter may be at least one of a current heart rate of the patient, a respiratory rate, a blood oxygen saturation, and a derivative parameter of a phonocardiographic signal or an endocardial acceleration signal. In one embodiment, the controller is configured to determine a current sleep stage based on the response of the patient to the stimulation. In some embodiments, the controller is configured to determine the stimulation energy that corresponds to a first sleep stage by initializing the stimulation energy to a predetermined default minimum value, comparing a current response of the patient to a first threshold, iteratively changing the stimulation energy until the stimulation energy exceeds the first threshold, and storing the stimulation energy for the first sleep stage. The controller may then determine and store the stimulation energy corresponding to each of the plurality of sleep stages following the first sleep stage based on the stimulation energy stored for the first sleep stage.

Another embodiment relates to a method of treating sleep apnea in a patient through stimulation. The method includes determining, by a controller, a sleep state of the patient, wherein the sleep state includes a plurality of sleep stages; modulating, by the controller, a stimulation energy of stimulation pulses produced by a generator based on the sleep stage of the patient; and delivering, by a stimulator, stimulation to the patient by receiving the stimulation pulses from the generator.

According to an exemplary embodiment, the generator is activated by the controller in the presence of the sleep state. The plurality of sleep stages include slow-wave sleep I, slow-wave sleep II, slow-wave sleep III, slow-wave sleep IV, and REM sleep. In one embodiment, the controller is configured to increase the stimulation energy as the sleep stage increases, and decrease the stimulation energy when the sleep stage increases.

In one embodiment, the method further includes detecting, by a sensor, an occurrence of an apnea or hypopnea episode; and activating, by the controller, the generator upon detection of the apnea or hypopnea episode. Additionally, the method may include detecting, by the sensor, an end of the apnea or hypopnea episode; and disabling, by the controller, the generator upon detection of the end of the apnea or hypopnea episode.

In various embodiments, the method includes determining, by the controller, a response of the patient to the stimulation based on the variation of a biological parameter of the patient following the delivery of the stimulation to the patient. The biological parameter may be at least one of a current heart rate of the patient, a respiratory rate, a blood oxygen saturation, and a derivative parameter of a phonocardiographic signal or an endocardial acceleration signal. In one embodiment, the method includes determining, by the controller, a current sleep stage based on the response of the patient to the stimulation. In another embodiment, the method includes determining, by the controller, the stimulation energy that corresponds to a first sleep stage by initializing the stimulation energy to a predetermined default minimum value; comparing a current response of the patient to a first threshold; iteratively changing the stimulation energy until the stimulation energy exceeds the first threshold; and storing the stimulation energy for the first sleep stage. In some embodiments, the controller is configured to determine and store the stimulation energy corresponding to each of the plurality of sleep stages following the first sleep stage based on the stimulation energy stored for the first sleep stage.

Still another embodiment relates to a device for treating sleep apnea in a patient. The device includes a generator configured to produce stimulation pulses; a stimulator that receives the stimulation pulses produced by the generator and delivers stimulation to the patient; and a controller configured to modulate a stimulation energy of the stimulation pulses produced by the generator based on a state of the patient during a sleep apnea or hypopnea episode.

DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

Figure 1:
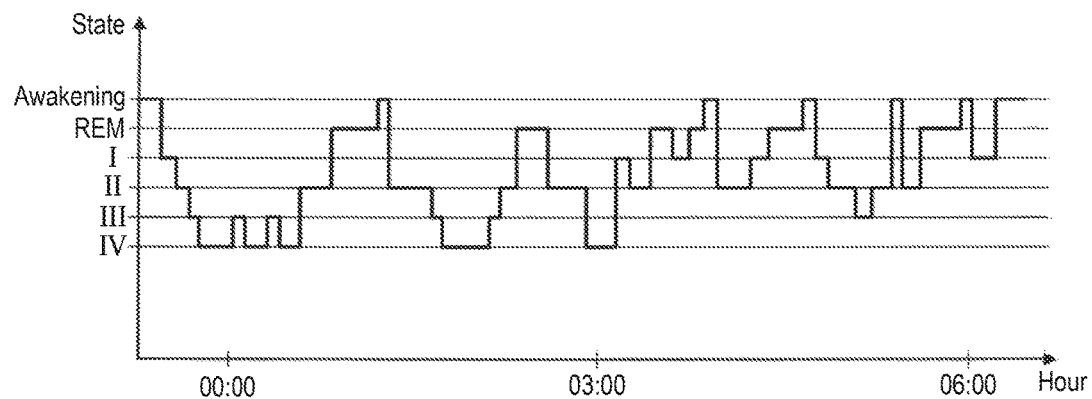
FIG. 1 illustrates in general the various successive stages during a night of a patient's sleep, according to an exemplary embodiment.

FIG. 1 is a diagram showing the different successive sleep stages of a patient during a night's sleep. This sleep is in the form of a series of cycles during which, from the waking state, the patient enters deeper and deeper cycles of slow wave sleep, from stage I (drowsiness) and II (light sleep) to stages III and IV (deep sleep). Then, usually after a short return to stage I, the patient enters a stage called REM (Rapid Eye Movements) sleep, which is characterized by high electrical activity of the brain. The cycles follow each other until the final morning awakening.

The different stages correspond to distinct forms of brain activity characterized by specific EEG tracings, recognizable on a record performed for example during polysomnography. The course of the sleep period of the patient can be interspersed by micro-awakenings. Depending on the importance of the micro-awakening, the patient may either return to the same stage, or be down from one stage or directly be boarded to a lighter sleep stage.

According to an exemplary embodiment, the kinesthetic stimulation device provides a non-invasive technique for determining, practically in real time, the current sleep stage of an asleep person without using an EEG examination (without setting up a multitude of electrodes on the patient's head) and with minimal or no risk of causing micro-awakenings that would be deleterious.

According to various embodiments, the kinesthetic stimulation device uses the current sleep stage information to modulate a kinesthetic stimulation, in particular so as to end episodes of sleep apnea (or hypopnea), without causing a patient micro-awakening, which would have negative consequences thereby losing any benefit to reducing apnea.

Figure 2:
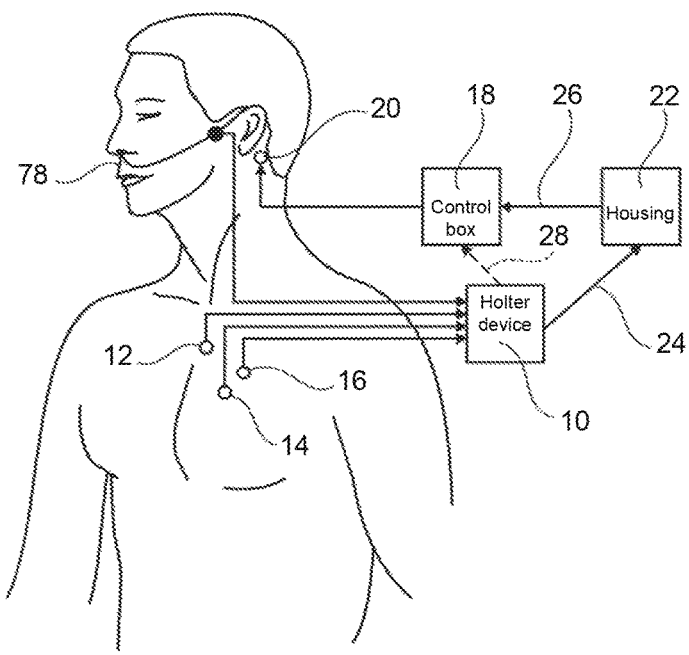
FIG. 2 schematically illustrates the main components of a kinesthetic stimulation system, according to an exemplary embodiment.

FIG. 2 schematically illustrates the main components of a system (e.g., a kinesthetic stimulation system, etc.) used for this purpose. This system includes a Holter recorder 10 connected to various sensors or electrodes 12, 14, 16, to measure physiological signals, such as heart rate, respiration, oxygen saturation, pulse wave, phonocardiogram, etc. In the following, we will focus mainly on the heart rate, which is a simple parameter to obtain, but this is not restrictive and the invention may be implemented from other physiological signals collected from the patient.

The system further includes a device for kinesthetic stimulation, with a generator housing including control box 18 producing pulses applied to kinesthetic stimulation effector 20, for example including of a vibrator disposed in a sensitive region of the skin, typically (in the adults) in the region of the mastoid bone in the vicinity of the ear. Vibrotactile stimulation applied to the skin by the effector 20 is detected by sensory receptors or mechanoreceptors in the body, and this information is then transmitted via the sensory nerves to the autonomous central nervous system.

The effector 20 is for example a transducer of the type C10-100 of Precision Microdrives or C2 Tactor of Engineering Acoustics. The type of transducer may be a transducer that weighs a few grams. The transducer may be capable of emitting vibrations through an integrated vibrator excited by pulse trains of varying amplitude and duration, typically at a frequency of 250 Hz which is the resonance nominal frequency of this particular effector and which is also the frequency at which the skin mechanoreceptors are the most sensitive. Other types of effectors can of course effectively be used.

The control box 18 is controlled by a microcontroller and is configured for adjusting the intensity (that is to say, energy) of kinesthetic stimulation, by controlled variation of the amplitude and/or the number, the duration and/or the frequency of the pacing pulse trains forming the signal applied to the effector 20.

The system also includes a housing 22 coupled to the Holter device 10 and to the control box 18 via a wire connection or wirelessly 24, 26 in order to receive data from the Holter device 10, process such data and generate control information of kinesthetic stimulation in response thereto to be transmitted to the control box 18. Alternatively, data processing and control of the control box 18 can be operated from within the Holter device 10 and transmitted by a link 28 to the housing 18.

Figure 3:
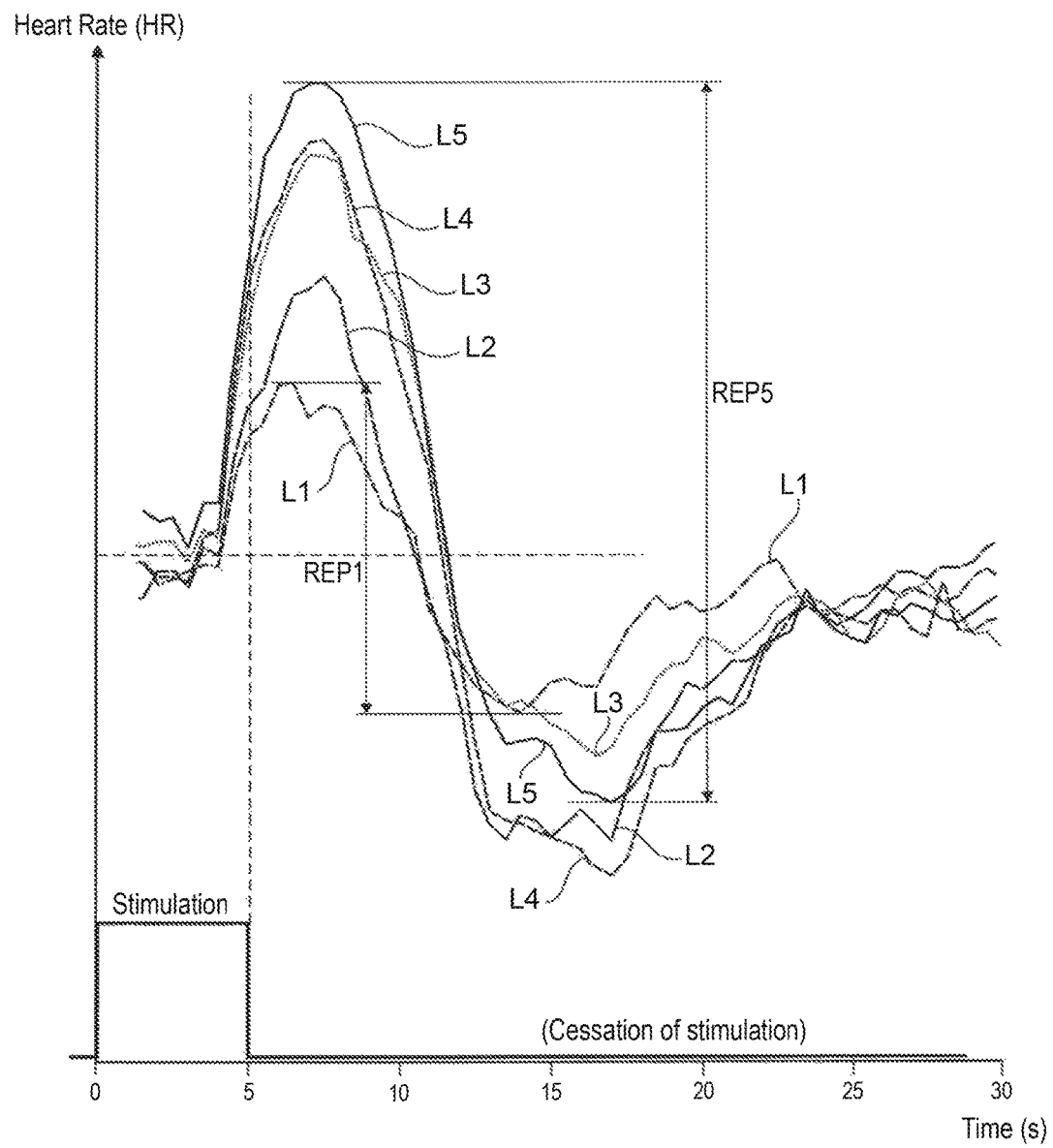
FIG. 3 illustrates the variations of the autonomic response to a kinesthetic stimulation pulse, this response being evaluated by the changes in the patient's heart rate, according to an exemplary embodiment.

FIG. 3 illustrates, in a given patient, the autonomic response to a kinesthetic stimulation, expressed here in terms of changes in heart rate. Such a measure is obtainable via the sensors 12, 14, 16. The acquisition of the heart rate is not limiting, as the methods may be implemented with other techniques for quantifying various other autonomic functions. For example, acquiring the blood pressure or heart sounds (by a phonocardiographic sensor or an endocardial acceleration sensor). The treatment is based on the kinesthetic stimulation applied in a sensitive area of the skin where the effector 20 may stimulate the autonomic pathways without generating a patient wake. Such an area may preferably be in the region of the ear. Responses to the stimulation of the autonomic system may thus be measured.

Thus, in a study related to patients with SAS data from two PSG recording nights, they were compared. Randomly, the patient spent a night without kinesthetic stimulation and the other night with kinesthetic stimulation of variable energy and applied at regular intervals. The analysis of these results showed that during nights with stimulation more autonomous micro-awakenings were observed, showing the effectiveness of the stimulation to activate the autonomic system. Furthermore, the duration of sleep and the duration of the various stages were not significantly different, indicating that the stimulation did not result in disintegration of sleep.

Changes in mean heart rate recorded for different levels of kinesthetic stimulation applied to the patient at any time during sleep (sleep stages all together) are shown in FIG. 3. At t=0, a burst of stimulation pulses is applied at a given energy level and then stopped at t=5s. Changes in heart rate induced by the stimulation, representative of the autonomic response of the patient, are illustrated by the characteristics L1 to L5, which correspond to increasing stimulation energies.

Typically, the response is biphasic, with an increase in heart rate followed by a decrease below the initial baseline, then back to an approximately stable frequency after twenty cycles after the end of the stimulus. This biphasic response is due to a sympathetic initial activation due to stimulation (increased heart rate), followed by a parasympathetic compensation response (deceleration curve). It can also be observed that the autonomic response, as measured on the characteristics L1-L5 by the respective amplitudes REP1-REP5 corresponding to the maximum excursion of the heart rate after stimulation, increases with the energy of this stimulation. The observation of the post-stimulation frequency change allows evaluating the significance of the autonomic response of the patient.

According to an exemplary embodiment, the treatment provided by the system relates to the use of measurable autonomic response for two purposes:

Determination of the sleep stage at a given time; and

Depending on the sleep stage thus determined, in the case of detected sleep apnea, the application of kinesthetic stimulation to stop apnea, but the energy of which is modulated according to the sleep stage in order not to cause micro-awakenings to the patient.

Figure 4:
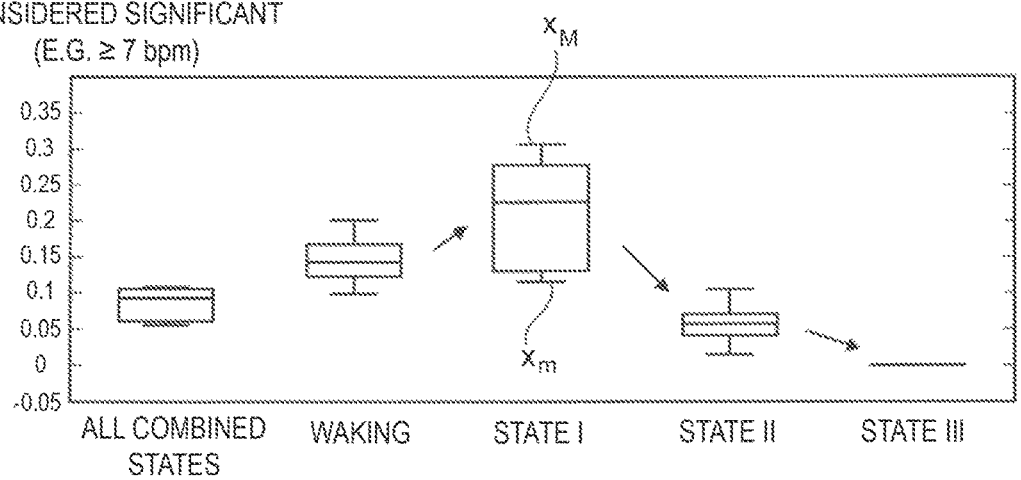
FIG. 4 is a diagram illustrating changes in the autonomic response of a population of patients at different sleep stages, for the same kinesthetic stimulation energy, according to an exemplary embodiment.
Figure 5:
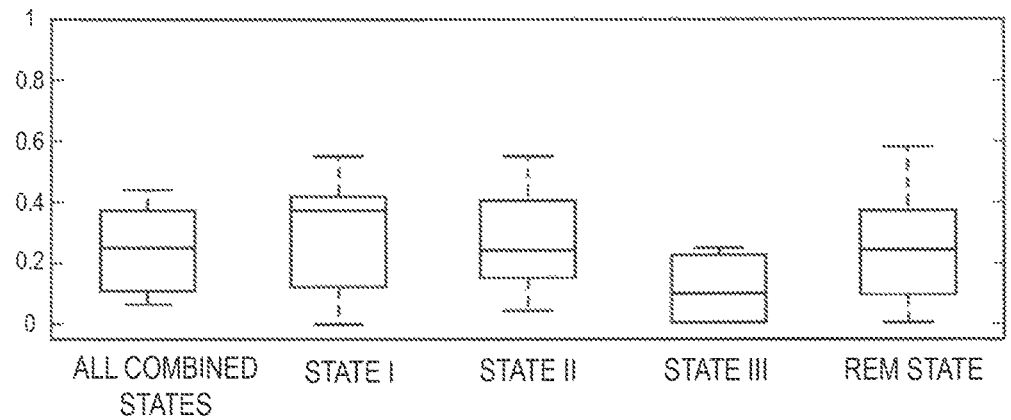
FIG. 5 is a diagram illustrating the proportion of effective micro-awakenings in a patient population according to the different sleep stages, for the same, maximum, kinesthetic stimulation energy, according to an exemplary embodiment.

FIGS. 4 and 5 show, in the form of box-plots, the results of a study on a population of patients on which the importance of the autonomic response (measured from the change in heart rate) in response to the application of a stimulation pulse kinesthetic was assessed, in various circumstances.

In FIG. 4, the vertical axis represents the response rate considered significant in the patient population (e.g. autonomic responses producing a heart rate excursion of at least 7 bpm) respectively in the following situations: all sleep stages combined, at the waking state, at the stage I sleep state, at the stage II sleep state, and at the stage III sleep state. It should be noted that, in the case of a population of patients with respiratory disorders such as sleep apnea, none reached the deepest stage IV.

In each of these situations, the central line represents the median of the samples and its position in the box is used to assess the symmetry of the data. The lower and upper lines of the box represent the empirical quartiles of order p=¼ (first quartile) and p=¾ (last quartile). The height of the box is thus the interquartile range. The two lines of the upper and lower limits show the maximum $x_M$ and minimum $x_m$ values identified for the considered case.

FIG. 4 shows that, for different sleep stages, the importance of the autonomic response following a kinesthetic stimulation decreases as the sleep stage becomes deeper (e.g., increases, etc.). The response during Stage II is lower than that during stage I, and that in stage III (which has been reached by only one patient in the study population) is lower than that in stage II. In other words, to trigger the same autonomic response, for example to stop a single apnea episode, the deeper the sleep stage is, the higher the kinesthetic stimulation energy may be.

In FIG. 5, with the same conventions as before, the micro-awakenings rate values (determined by a polysomnographic analysis, for example) for the same sleep stages as those in FIG. 5 are illustrated: all cumulated sleep stages, stage I, II, III and REM. It is shown that the micro-awakenings rate also depends on the sleep stage. For a given energy, the more the sleep stage corresponds to a deep sleep, the more the micro-awakenings rate decreases. It will be possible to increase the energy of the kinesthetic stimulation when the sleep stage moves to a deeper level, without the risk of increasing the micro-awakenings. In other words, the energy of stimulation may be increased when the stage increases, to ensure the effectiveness of the response; conversely, when a light stage is detected again, the stimulation energy has to be reduced again to avoid causing a wake of the patient.

Determination of the Current Sleep Stage

The determination of the sleep stage of the patient at a given time can be advantageously used for the therapy of sleep apnea, by appropriately modulating kinesthetic stimulation so as not to induce micro-awakenings. This use, however, is not limitative and the detection of sleep stages may be used for other therapeutic purposes or other diagnostic purposes, for example, an analysis by simple methods of the course of a night's sleep in a patient so as to have a record of the successive stages over time, including whether the patient sleep reaches the deepest, most restorative, stages or if an underlying disorder prevents him from reaching these stages.

Figure 6:
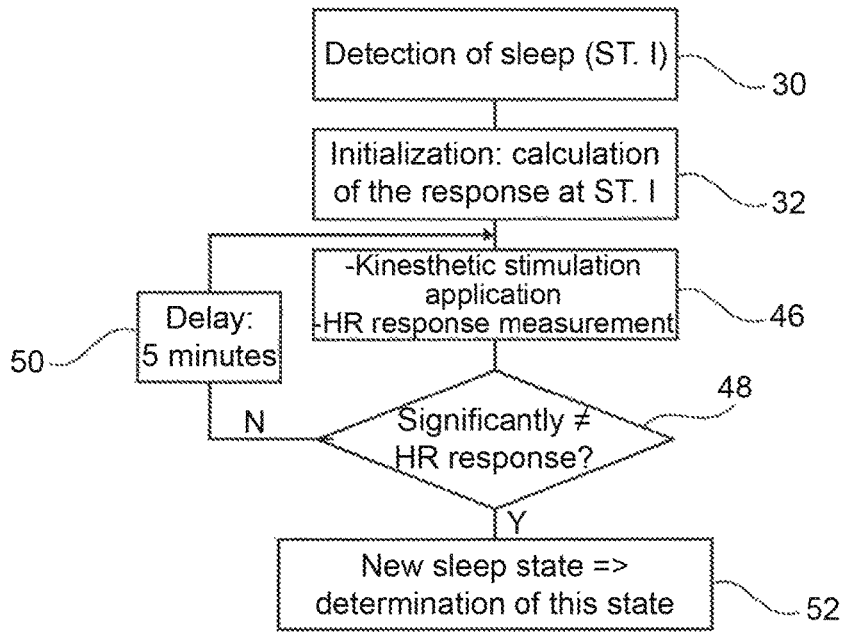
FIGS. 6 and 7 are flow charts illustrating the different steps implemented by the technique of automatic detection of sleep stages, according to an exemplary embodiment.
Figure 7:
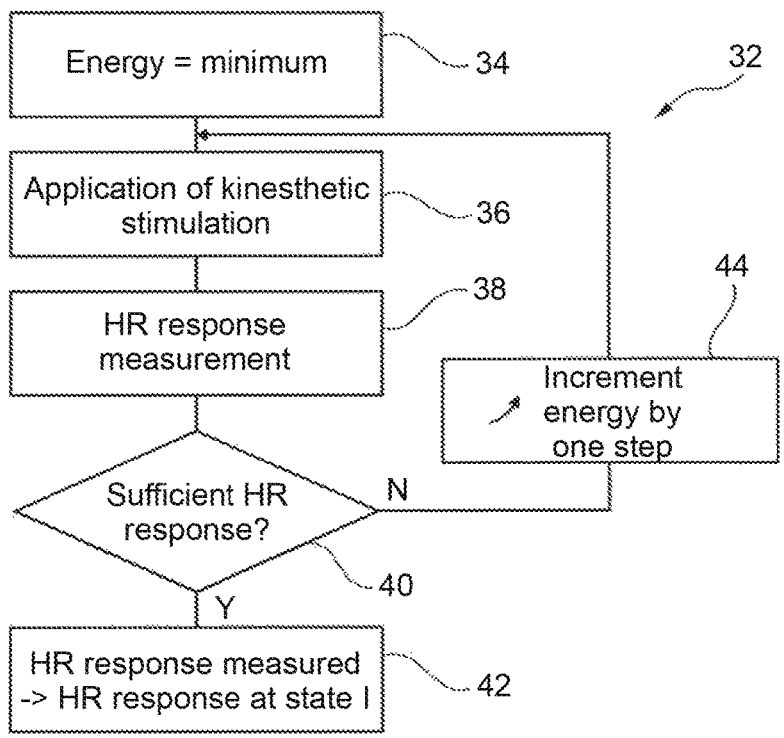

With reference to FIGS. 6 and 7, an exemplary implementation of the method is described, for automatically determining sleep stages based on the autonomic response to a kinesthetic stimulation. The algorithm begins with a search for the patient to detect his falling asleep thereof, that is to say, the transition from waking to stage I sleep state (step 30). This detection of the sleep/wake state of the patient may be effected for example by a known technique of overlap of information delivered by a physiological sensor (minute ventilation sensor, MV) and an activity sensor (accelerometer sensor, G), with monitoring of the heart rate. Such a technique is described for example in EP 1317943 A1 (Sorin CRM S.A.S previously known as ELA Medical).

After falling asleep is detected, the patient is necessarily in stage I. Therefore, an initialization of the autonomic response corresponding to the first stage is carried out (step 32). This initialization of step 32 is described in more detail in FIG. 7. First, the energy of kinesthetic stimulation is initialized to the minimum level allowed by the kinesthetic effector stimulation (step 34). A first stimulation is applied (step 36) and the autonomic response is measured, typically by measuring the deflection of the heart rate (HR) following the application of the pulse (step 38). If the heart rate variation is sufficient (test 40), for example at least 7 bpm, then the applied energy is saved and stored for the night and the measured HR response is recorded as corresponding to the response at the stage I (step 42). Heart rate variation is considered sufficient when it results in a variation of the autonomic response to this stage and to the next stage— because the autonomic response decreases when the stage increases.

In the case when the observed response is not sufficient, then the energy is increased by one step (step 44) and the method is repeated (steps 36 and following) with the new stimulation energy. In another implementation, the step 36 may include a group of stimulation in order to obtain an average autonomic response, or stimulation with two different energies, to verify a variation in frequency between the different energies is obtained.

Referring back to FIG. 6, after the initialization (step 32), periodically or when it is optimal to estimate the current sleep stage, kinesthetic stimulation is applied with the energy that has just been determined, and the autonomic response is measured (step 46). If the HR response did not significantly change (test 48), no special action is undertaken and the method is repeated periodically (typically every five minutes, timing of step 50). In the same method as for step 36, step 46 may also include a group of stimuli, the evaluation of the step 48 then being made on the average of the observed responses.

If, however, the level of the autonomic response is significantly varied (test 48) compared to the previously tested and stored level, this indicates that the sleep stage was probably changed and the new stage has to be determined (step 52). The new sleep stage is determined both i) depending on the HR response, that is to say the variation in heart rate observed in response to the stimulation, and ii) according to the recent history sleep stages in of the patient.

To this end, in a first determination approach, it will be considered that a reduction in the HR response reveals the transition into a deeper sleep, while an increase of this response reveals the transition to a lighter sleep. The significance of this decrease/increase may also be used to assess the sleep stage based on data from statistical studies on a patient population, studies that have evaluated typical decreased/increased amplitudes according to different transitions: stage I/stage II, stage II/stage III, stage III/stage I, etc. Data from a preliminary study thus showed that the HR response decreases by an average of 18% between stage I and II, of 20% between stage I and III and of 10% between stage I and REM stage. However, a transition to wakefulness causes an increase of 22% of the HR response.

Another approach is a stochastic, Markov and semi-Markov, approach. The hidden Markov models are automata with a finite state number stochastically and non-deterministically describing a system. The basic structure of a Markov model includes of a set of states S=(S1, S2 . . . SN) connected to each other by a probability defined in a transition table. The adjective "hidden" here translates the fact that the issuance of observations from a state follows a random relationship and that the underlying method (sleep stage) is not directly observable (it is "hidden"). This random characteristic of the measures which, added to the properties of the Markov processes, provides the flexibility and power of this approach. In the case of first-order models, the system state at time t depends only on the state of the system at time t-1, which defines a pure Markov process. Hidden semi-Markov models are similar to Markov models, but the system state at time t depends not only on the state at t-1, but also of other parameters such as the length of stay in the current state.

In the approach proposed here, each state of the Markov or semi-Markov model is a sleep stage and the probability of transition from one stage to another depends on both observable phenomenon (autonomic response) and on a transition probabilities matrix learned from a database, such as that already established in the studies cited above. This type of model estimates, given the observable phenomenon and the learned transition matrix, the state of a system at any time t.

Dependence of the kinesthetic stimulation based on sleep stages

Figure 8:
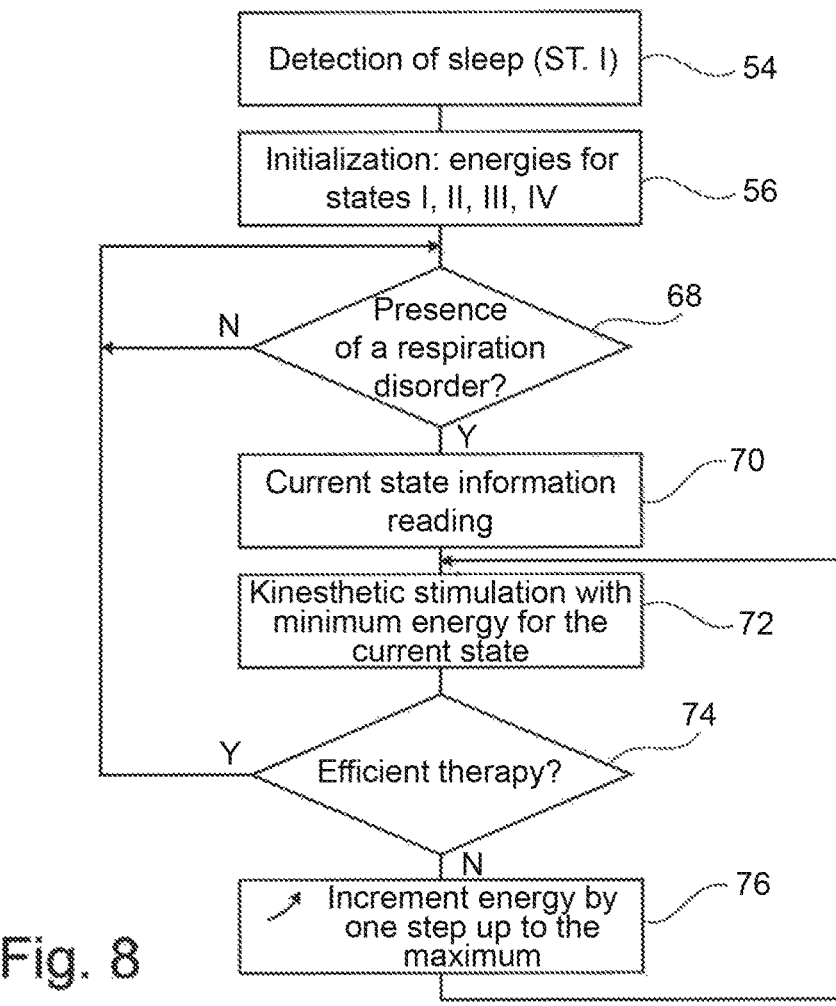
FIGS. 8 and 9 are diagrams illustrating the various successive steps implemented by the servo technique of the invention of the kinesthetic stimulation depending on the sleep stage, according to an exemplary embodiment.
Figure 9:
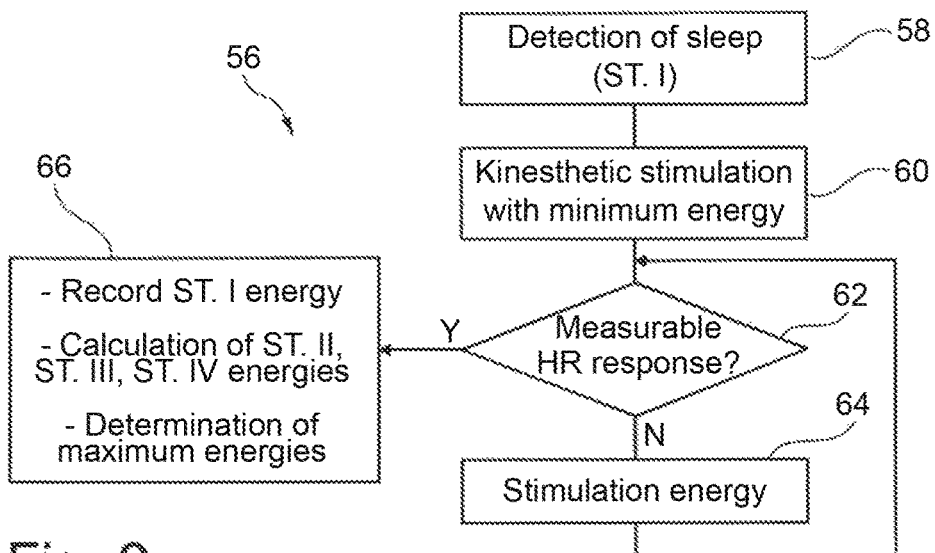

The algorithm of FIGS. 8 and 9 shows an example of treatment of respiratory disorders of sleep apnea or hypopnea type per modulated kinesthetic stimulation depending on the current sleep stage of the patient, according to an exemplary embodiment.

The algorithm starts with the detection of the falling asleep of the patient (step 54) according to a similar technique to the one described above in step 30 of FIG. 6 for the discrimination between the various sleep stages. After the falling asleep is detected, the patient is now in stage I, and the stimulation energy of the various stages are then initialized (step 56).

A first technique may provide fixed values, progressively increasing as the stages become deeper, to the stimulation energy of the different stages. These values can be the same for all patients (values calculated from averages of clinical observations), or can be individualized after preliminary assessment during polysomnography. These values can also be initialized from a first efficient energy (calculated in step 42 in FIG. 7) and then changes in relative variation (percentage) or absolute variation ("delta") of the first value for the other sleep stages can be calculated, these variations being directly collected from clinical observations.

Another technique is to apply the minimum stimulation as determined in step 42 of FIG. 7. When it is detected that the stage is changed, the energy of the stimulation must be modified. If the stage is deeper, energy is increased to find a significant change in heart rate parameter. If the stage is lighter, the energy level starts from the minimum energy and back.

Specifically, the initialization step is illustrated in FIG. 9, once the sleep is detected (step 58 identical to step 54 of FIG. 8) a first stimulation is applied with the minimum energy (step 60). If a measurable response is not detected (test 62), then the stimulation energy is increased by one step (step 64) and the stimulation is repeated until a measurable response is found. The energy thus adjusted is stored as the effective energy corresponding to stage I (step 66). The energies corresponding to the other stages are determined from this value, either by adding a fixed value or by increasing it by a predetermined rate. During the initialization phase 56, we can also determine the maximum stimulation energy value beyond which a wake is to be feared and this for each sleep stage. This maximum value can be derived from energies evaluated for the different stages by adding a predetermined margin, or may have been determined in a prior polysomnography.

Back to FIG. 8, once the initialization is completed (step 56), the algorithm enters into a research phase of the emergence of a respiratory disorder (step 68). Various methods of detection of the occurrence of an apnea or hypopnea has been described for example in EP 1319421 A1, EP 1433496 A1 or EP 1584288 A1, all three in the name of Sorin CRM S.A.S, previously known as ELA Medical, each of which is incorporated herein in their entireties.

These documents may be referred to for more details on the method to operate the detection and diagnosis of sleep disorders. It is also possible, if the patient is not implanted, to use a nasal cannula (78 in FIG. 2) with an appropriate sensor for directly detecting the interruption of the normal respiratory flow.

As soon as a condition is detected, the algorithm determines the current sleep stage (step 70), this information being obtained in particular by implementation of the algorithm described above with reference to FIGS. 6 and 7. Kinesthetic stimulation is then delivered (step 72) with the energy which had been determined for the current sleep stage, during the initialization step 56. The effectiveness of kinesthetic stimulation is evaluated (step 74), that is to say, the device determines if the therapy that has been applied has been effective or not. This efficiency can be assessed during the event, immediately, that is to say it is observed whether we are in the presence of a characteristic episode of debut of apnea followed by a rapid recovery of breathing revealing the apnea stop consecutive to kinesthetic stimulation.

Another method to evaluate the effectiveness of the therapy is, alternatively or in addition, to make a count of the number of events indicative of a respiratory disorder in a given period, for example 5 or 10 minutes, and to check if, based on a history, this count indicates a decrease in the severity of symptoms or not.

In any event, if the therapy was not effective, the stimulation energy is increased by one step (step 76), and this up to a predetermined maximum corresponding to the limit that could cause a micro-awakening, therefore with the risk that the treatment itself produce deleterious effects.

The invention claimed is:

1. A device for treating sleep apnea in a patient through stimulation, comprising:
   a generator configured to produce stimulation pulses;
   a stimulator configured to receive the stimulation pulses produced by the generator and deliver stimulation to the patient; and
   a controller configured to:
   detect a presence of sleep apnea;
   determine a sleep state of the patient;
   determine a response of the patient to the stimulation produced by the generator and an effectiveness of the stimulation based on the response;
   adaptively control the generator based on the sleep state and the presence of the sleep apnea, wherein the sleep state includes a plurality of sleep stages; and
   modulate a stimulation energy of the stimulation pulses produced by the generator based on the sleep stage of the patient and the presence of the sleep apnea, the controller configured to increase the stimulation energy of the stimulation pulses in response to the stimulation pulses being ineffective in treating the sleep apnea to a level sufficient to stop the sleep apnea and low enough to limit an occurrence of micro-awakenings of the patient.

2. The device of claim 1, wherein the controller is further configured to activate the generator in the presence of the sleep state, and wherein the plurality of sleep stages include slow-wave sleep I, slow-wave sleep II, slow-wave sleep III, slow-wave sleep IV, and REM sleep.

3. The device of claim 1, wherein the controller is configured to increase the stimulation energy as the sleep stage increases, and decrease the stimulation energy as the sleep stage decreases.

4. The device of claim 1, further comprising a sensor configured to detect an occurrence of an apnea or hypopnea episode, wherein the controller activates the generator upon detection of the apnea or hypopnea episode.

5. The device of claim 4, wherein the sensor is configured to detect an end of the apnea or hypopnea episode, wherein the controller disables the generator upon detection of the end of the apnea or hypopnea episode.

6. The device of claim 1, wherein the controller modulates the stimulation energy based on a predetermined increment/decrement for each of the plurality of sleep stages.

7. The device of claim 1, wherein the controller utilizes a correspondence table to assign the stimulation energy to each of the plurality of sleep stages.

8. The device of claim 1, wherein the controller determines the response of the patient to the stimulation based on the variation of a biological parameter of the patient following the delivery of the stimulation to the patient, wherein the biological parameter is at least one of a current heart rate of the patient, a respiratory rate, a blood oxygen saturation, or a derivative parameter of a phonocardiographic signal or an endocardial acceleration signal.

9. The device of claim 8, wherein the controller is configured to determine a current sleep stage based on the response of the patient to the stimulation.

10. The device of claim 8, wherein the controller is configured to determine the stimulation energy that corresponds to a first sleep stage by:
   initializing the stimulation energy to a predetermined default minimum value;
   comparing a current response of the patient to a first threshold;
   iteratively changing the stimulation energy until the stimulation energy exceeds the first threshold; and
   storing the stimulation energy for the first sleep stage.

11. The device of claim 10, wherein the controller is configured to determine and store the stimulation energy corresponding to each of the plurality of sleep stages following the first sleep stage based on the stimulation energy stored for the first sleep stage.

12. A method of treating sleep apnea in a patient through stimulation, comprising:
   detecting, by a controller, a presence of sleep apnea;
   determining, by the controller, a sleep state of the patient, wherein the sleep state includes a plurality of sleep stages;
   determining, by the controller, a response of the patient to stimulation pulses produced by a generator and an effectiveness of the stimulation pulses based on the response;
   modulating, by the controller, a stimulation energy of the stimulation pulses produced by the generator based on the sleep stage of the patient and the presence of the sleep apnea, including increasing the stimulation energy of the stimulation pulses in response to the stimulation pulses being ineffective in treating the sleep apnea to a level sufficient to stop the sleep apnea and low enough to limit an occurrence of micro-awakenings of the patient; and
   delivering, by a stimulator, the modulated stimulation pulses received from the generator to the patient.

13. The method of claim 12, further comprising activating, by the controller, the generator in the presence of the sleep state, and wherein the plurality of sleep stages include slow-wave sleep I, slow-wave sleep II, slow-wave sleep III, slow-wave sleep IV, and REM sleep.

14. The method of claim 12, wherein modulating the stimulation energy of the stimulation pulses comprises increasing the stimulation energy as the sleep stage increases, and decreasing, by the controller, the stimulation energy as the sleep stage decreases.

15. The method of claim 12, further comprising:
   detecting, by a sensor, an occurrence of an apnea or hypopnea episode; and
   activating, by the controller, the generator upon detection of the apnea or hypopnea episode.

16. The method of claim 15, further comprising:
   detecting, by the sensor, an end of the apnea or hypopnea episode; and
   disabling, by the controller, the generator upon detection of the end of the apnea or hypopnea episode.

17. The method of claim 12, further comprising determining, by the controller, the response of the patient to the stimulation pulses based on the variation of a biological parameter of the patient following the delivery of the stimulation pulses to the patient, wherein the biological parameter is at least one of a current heart rate of the patient, a respiratory rate, a blood oxygen saturation, and a derivative parameter of a phonocardiographic signal or an endocardial acceleration signal.

18. The method of claim 17, further comprising determining, by the controller, a current sleep stage based on the response of the patient to the stimulation pulses.

19. The method of claim 17, further comprising determining, by the controller, the stimulation energy that corresponds to a first sleep stage by:
   initializing the stimulation energy to a predetermined default minimum value;
   comparing a current response of the patient to a first threshold;
   iteratively changing the stimulation energy until the stimulation energy exceeds the first threshold;
   storing the stimulation energy for the first sleep stage; and
   determining and storing the stimulation energy corresponding to each of the plurality of sleep stages following the first sleep stage based on the stimulation energy stored for the first sleep stage.

20. A device for treating sleep apnea in a patient, comprising:
   a generator configured to produce stimulation pulses;
   a stimulator configured to receive the stimulation pulses produced by the generator and deliver stimulation to the patient; and
   a controller configured to:
      determine a response of the patient to the stimulation pulses produced by the generator and an effectiveness of the stimulation pulses based on the response; and
      modulate a stimulation energy of the stimulation pulses produced by the generator based on a sleep stage of the patient during a sleep apnea or hypopnea episode, the controller configured to increase the stimulation energy of the stimulation pulses in response to the stimulation pulses being ineffective in treating the sleep apnea or hypopnea episode to a level sufficient to stop the sleep apnea or hypopnea episode and low enough to limit an occurrence of micro-awakenings of the patient.

* * * * *